(12) United States Patent
Mine et al.

(10) Patent No.: US 7,161,041 B2
(45) Date of Patent: Jan. 9, 2007

(54) PROCESS FOR PRODUCING CYCLOALKANONE DERIVATIVES

(75) Inventors: Koji Mine, Wakayama (JP); Kimikazu Fukuda, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/735,737

(22) Filed: Dec. 16, 2003

(65) Prior Publication Data

US 2004/0171850 A1 Sep. 2, 2004

(30) Foreign Application Priority Data

Dec. 26, 2002 (JP) ............... 2002-378005

(51) Int. Cl.
*C07C 45/48* (2006.01)
(52) U.S. Cl. ..................................... 568/313
(58) Field of Classification Search ................ 568/313
See application file for complete search history.

(56) References Cited

FOREIGN PATENT DOCUMENTS

| EP | 0 033 604 | 8/1981 |
|---|---|---|
| EP | 1 316 541 | 6/2003 |
| GB | 2 146 995 | 5/1995 |
| JP | 2001-335529 | 12/2001 |

*Primary Examiner*—Taofiq Solola
(74) *Attorney, Agent, or Firm*—Oblon, Spivak, McClelland, Maier & Neustadt, P.C.

(57) ABSTRACT

The present invention provides a process for producing 2-(1-hydroxyalkyl)cycloalkanone and/or 2-(1-hydroxyaryl) cycloalkanone in high yield and selectivity, as well as a process using the same to produce a cycloalkanone derivative useful as a perfume material and a physiologically active substance. Disclosed is a process for producing compound (3), which includes subjecting a cycloalkanone, and aldehyde (2) containing carboxylic acid (1), to aldol condensation in the presence of water and a basic catalyst, wherein the molar amount (referred to hereinafter as A) of the basic catalyst added is not less than the molar amount (referred to hereinafter as B) of the carboxylic acid (1) contained in the aldehyde (2) and the difference between A and B, that is, (A–B) is 0.06 mol or less per mol of the aldehyde (2), as well as a process for producing compounds (7) and (8) by using the compound (3) obtained by the above process.

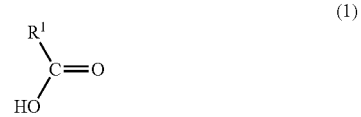

(1)

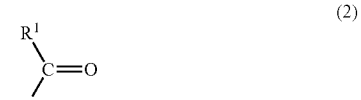

(2)

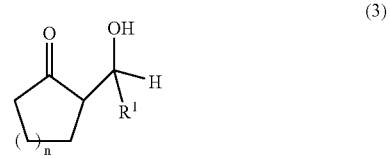

(3)

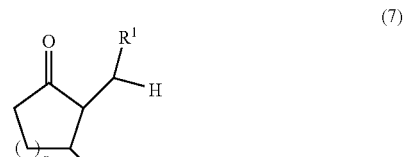

(7)

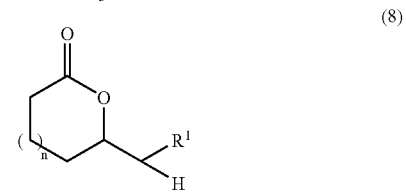

(8)

wherein n is an integer of 1 or 2, $R^1$ represents H or a C1 to C8 alkyl group or the like, and $R^2$ represents a C1 to C3 alkyl group.

2 Claims, No Drawings

PROCESS FOR PRODUCING CYCLOALKANONE DERIVATIVES

TECHNICAL FIELD

The present invention relates to a process for producing 2-(1-hydroxyalkyl)cycloalkanone and/or 2-(1-hydroxyaryl) cycloalkanone useful as an intermediate for synthesis of a physiologically active substance and a perfume, a process using the same to produce alkyl (3-oxo-2-alkylcycloalkyl) acetate and/or alkyl (3-oxo-2-arylcycloalkyl)acetate useful as a perfume material and a physiologically active substance, and a process for producing 5-alkyl-5-alkanolide and/or 5-aryl-5-alkanolide.

BACKGROUND ART

JP-A 56-147740 describes a process for producing 2-(1-hydroxyalkyl)cycloalkanone wherein a cycloalkanone and an alkyl aldehyde are subjected to aldol condensation by using a basic catalyst in an amount of about 0.05 to 0.1 mol per mol of alkyl aldehyde, and JP-A 2001-335529 describes a process for producing the same by aldol condensation using a basic catalyst in an amount of 0.04 mol or less per mole of alkyl aldehyde.

However, the alkyl aldehyde is inherently easily oxidized to form an alkylcarboxylic acid, and this alkylcarboxylic acid is reacted with the basic catalyst during aldol condensation to reduce the catalytic activity significantly, thus significantly lowering the yield and selectivity in many cases. For preventing such oxidation, a method of storing and using the alkyl aldehyde by sealing with nitrogen is adopted, but oxidation proceeds gradually to make contamination with an alkylcarboxylic acid inevitable.

In the processes described in JP-A 56-147740 and JP-A 2001-335529 supra, a cycloalkanone is used in excess of an alkyl aldehyde, and thus the unreacted cycloalkanone remains after the reaction. The cycloalkanone is dissolved in a large amount in the aqueous layer used in the reaction so that if the aqueous layer is discarded after one reaction, the unreacted remaining cycloalkanone will be lost in a large amount, thus increasing an environmental impact.

SUMMARY OF INVENTION

The present invention provides a process for producing 2-(1-hydroxyalkyl)cycloalkanone and/or 2-(1-hydroxyaryl) cycloalkanone represented by formula (3) (referred to hereinafter as compound (3)), which includes subjecting a cycloalkanone, and an aldehyde represented by formula (2) (referred to hereinafter as aldehyde (2)) containing a carboxylic acid represented by formula (1) (referred to hereinafter as carboxylic acid (1)), to aldol condensation in the presence of water and a basic catalyst, wherein the molar amount (referred to hereinafter as A) of the basic catalyst added is not less than the molar amount (referred to hereinafter as B) of the carboxylic acid (1) represented by formula (1) (referred to hereinafter as carboxylic acid (1)) contained in the aldehyde (2) and the difference between A and B, that is, (A–B) is 0.06 mol or less per mol of the aldehyde (2).

The invention relates also to a process for producing the compound (3) wherein an aqueous layer obtained by the aldol condensation reaction may be repeatedly used.

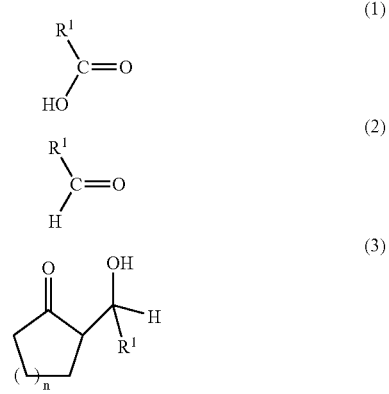

wherein n is an integer of 1 or 2, and $R^1$ represents a hydrogen atom or a C1 to C8 linear or branched alkyl group or a substituted or unsubstituted aryl group.

Further, the present invention provides a process for producing an alkyl (3-oxo-2-alkylcycloalkyl)acetate and/or an alkyl (3-oxo-2-arylcycloalkyl)acetate, represented by formula (7) (referred to hereinafter as compound (7)):

(7)

wherein n and $R^1$ have the same meaning as defined above and $R^2$ is a C1 to C3 linear or branched alkyl group, which includes dehydrating the compound (3) obtained by the method described above, to give a 2-(alkylidene)cycloalkanone and/or a 2-(arylene) cycloalkanone represented by formula (4) (referred to hereinafter as compound (4)):

(4)

wherein n and $R^1$ have the same meaning as defined above, then isomerizing the compound (4) to give a 2-(alkyl) cycloalkenone and/or a 2-(aryl)cycloalkenone represented by formula (5) (referred to hereinafter as compound (5)):

(5)

wherein n and $R^1$ have the same meaning as defined above, then reacting the compound (5) with a malonic diester represented by formula (6):

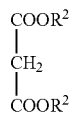  (6)

(in which $R^2$ has the same meaning as defined above and two $R^2$ groups may be the same as or different from each other, and reacting the product with water to give the compound (7).

The present invention provides a process for producing a 5-alkyl-5-alkanolide and/or a 5-aryl-5-alkanolide represented by formula (8) (referred to hereinafter as compound (8)):

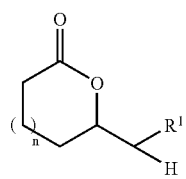  (8)

wherein n and $R^1$ have the same meaning as defined above, which includes dehydrating the compound (3) to give the compound (4), subsequently isomerizing it to give the compound (5) and hydrogenating it, followed by Baeyer-Villiger oxidation.

DETAILED EXPLANATION OF THE INVENTION

The present invention relates to provide a process for producing 2-(1-hydroxyalkyl)cycloalkanone and/or 2-(1-hydroxyaryl)cycloalkanone stably in high yield and high selectivity regardless of the content of carboxylic acid in aldehyde, a process for producing 2-(1-hydroxyalkyl)cycloalkanone and/or 2-(1-hydroxyaryl)cycloalkanone by using a cycloalkanone effectively to reduce an environmental impact, and a process using the same to produce a cycloalkanone derivative useful as a perfume material and a physiologically active substance.

The present inventors have found that 2-(1-hydroxyalkyl)cycloalkanone and/or 2-(1-hydroxyaryl)cycloalkanone can be obtained stably in high yield and high selectivity regardless of the content of carboxylic acid in aldehyde by controlling the adding amount of a basic catalyst to be an equimolar amount or more relative to the carboxylic acid contained in the aldehyde and to be a specific amount or less relative to the aldehyde so as to carry out a reaction.

The present inventors have also found that the aqueous layer used in the reaction is repeatedly used, whereby the cycloalkanone can be efficiently used while waste water can be reduced, thus leading to a reduction in environmental impact. The present inventors found through their study that when the aqueous layer is used again after pH adjustment with an acid and separation of the layer, the reaction yield is reduced upon accumulation of a large amount of neutral salts, but this reduction can be prevented by limiting the amount of the basic catalyst used in one reaction to the minimum amount for allowing the reaction to proceed.

According to the process of the present invention, a cycloalkanone and the aldehyde (2) containing the carboxylic acid (1) are used as the starting materials to produce the compound (3) stably in high yield and high selectivity regardless of the content of the carboxylic acid (1) in the aldehyde (2), and simultaneously the cycloalkanone can be effectively used thus reducing waste water thereby reducing an environmental impact. Further, the resulting compound (3) can be used to efficiently produce the compounds (7) and (8) useful as perfume materials and physiologically active substances.

[Process for Producing the Compound (3)]

The cycloalkanone used in the process for producing the compound (3) in the present invention is cyclopentanone or cyclohexanone, preferably cyclopentanone. The aldehyde (2) is preferably an aldehyde wherein $R^1$ is preferably a C1 to C8 alkyl group, more preferably a C3 to C5 alkyl aldehyde. The aldehyde (2) is still more preferably an aldehyde (valeraldehyde) having a C4 linear alkyl group.

The aldehyde (2) used in the present invention contains its oxide i.e. the carboxylic acid (1). The method of quantifying the carboxylic acid (1) in the aldehyde (2) includes, for example, liquid chromatography, gas chromatography, titration, etc., but in consideration of convenience, acid value determined by titration is desirably used.

The basic catalyst used in the present invention is preferably a compound represented by formula (9):

$$M(OH)_m \tag{9}$$

wherein M is an alkali metal such as Li, Na and K or an alkaline earth metal such as Mg, Ca and Ba, preferably an alkali metal, and m is an integer of 1 or 2.

In the present invention, the amount (A) of the basic catalyst added is not less than the amount (B) of the carboxylic acid (1) contained in the aldehyde (2) (i.e., the amount (A) is not less than the equimolar amount of the carboxylic acid (1)), and the difference between A and B, that is, (A–B) is 0.06 mol or less, preferably 0 to 0.02 mol, more preferably 0.001 to 0.005 mol, per mol of the aldehyde (2), from the viewpoint of achieving good reaction rate and yield.

The amount (B) of the carboxylic acid (1) contained in the aldehyde (2) corresponds to the number of moles of KOH for the acid value (mg-KOH/g) of the aldehyde (2). That is, a required mole number of KOH is determined from the acid value (mg-KOH/g) of the aldehyde (2) and the amount of the aldehyde (2), and the basic catalyst in an amount of not less than the equimolar amount of the required mole number of KOH can be added to prevent a reduction in yield and selectivity. The difference between A and B (A–B); that is, the amount (A) of the basic catalyst added minus the amount (corresponding to B) of the basic catalyst reacting with the carboxylic acid (1)) is the amount of the basic catalyst effective for allowing the reaction to proceed, and (A–B) can be made 0.06 mol or less per mol of the aldehyde (2) to prevent formation of byproducts such as cycloalkanone dimers. Even if the aqueous layer is repeatedly used, high yield can be maintained.

Further, in the process of the present invention, the ratio by weight of added water to the cycloalkanone is preferably 0.2 to 1.2, more preferably 0.4 to 1.2, especially preferably 0.4 to 0.6, from the viewpoint of preventing formation of byproducts such as aldehyde (2) dimers, cycloalkanone dimers, and high-boiling components.

The cycloalkanone is reacted with the aldehyde (2) such that the molar ratio of the cycloalkanone to the aldehyde (2)

is preferably 1 or more from the viewpoint of higher yield, more preferably 1.2 to 4.0, still more preferably 1.2 to 3.0, especially 1.5 to 2.7 mol, from the viewpoint of recovery of an excess of the cycloalkanone.

The reaction temperature of the aldol condensation is preferably −5 to 40° C., more preferably −5 to 30° C., from the viewpoint of prevention of coagulation of the aqueous layer and prevention of formation of cycloalkanone dimers etc.

It is desired in the process of the present invention that the cycloalkanone, water and the basic catalyst are charged into a reactor, and while the mixture is kept at the reaction temperature described above, the aldehyde (2) is added dropwise thereto. The dropping time does not affect the yield, and may be changed depending on the temperature-controlling ability of the reactor. After the aldehyde (2) is added, aging reaction may be carried out if necessary to increase the degree of conversion. The aging time is not particularly limited, and as the time is increased, byproducts are gradually increased. In consideration of productivity, it is desired that the time of dropping the aldehyde (2) is about 1 to 8 hours, and the aging time is about 1 to 6 hours. This reaction is conducted preferably in an inert gas atmosphere. The inert gas includes nitrogen, argon, etc.

The pressure of the aldol condensation reaction, in terms of absolute pressure, is preferably 10 kPa to 1 MPa, more preferably 50 to 300 kPa, still more preferably more or less than 100 kPa.

Because the aldol condensation reaction is a reaction in a two-layer system of cycloalkanone and water, use of a solvent destroying this system is not preferable. The solvent used in the present invention is not particularly limited, provided that it is inert to the reaction system and does not hinder separation and purification of the product, and such solvents include those having a boiling point in the range of 140 to 210° C., such as aromatic hydrocarbon solvents (benzene, toluene, etc.) and aliphatic hydrocarbon solvents (nonane, decane, undecane, etc.).

Because the aqueous layer used in the aldol condensation reaction contains a large amount of the cycloalkanone, the aqueous layer is preferably separated and repeatedly used. Because a part of the aqueous layer is distributed in the oil layer, its corresponding amount of water and a basic catalyst may further be added in the reaction for repeated use. If necessary, they may further be added.

In the presence of the basic catalyst, separation of the layer may be time-consuming. In this case, the layer may be separated for repeated use after adjustment with an acid to pH at which the layer can be easily separated. When it is also necessary to recover the cycloalkanone by distillation from the oil layer after separation of the layer, the pH value is regulated desirably in the acidic range, preferably in the range of pH 4 to 7, in order to prevent decomposition of the compound (3).

The acid used here is not particularly limited, and general organic acids and inorganic acids can be used, but in respect of easy handling, costs, etc., the acid is preferably sulfuric acid, phosphoric acid or condensed phosphoric acid.

When the acid is added, it is desirable to add, besides the above-described amount of the basic catalyst, the basic catalyst in such an amount as to neutralize or alkalize (to pH 7 or more) the aqueous layer in order to use the aqueous layer again in the reaction.

[Process for Producing the Compound (7)]

Using the compound (3) obtained by the above process as the starting material, the compound (7) useful as a perfume material and a physiological activator can be obtained by a method described in e.g. JP-A 56-147740.

Specifically, the compound (3) is subjected to dehydration reaction with oxalic acid or the like to give compound (4) which is then subjected to isomerization reaction in the presence of an aqueous acid (hydrochloric acid or hydrobromic acid) in n-butanol under reflux to give the compound (5). Then, the compound (5) is reacted with the compound (6) in the presence of a basic catalyst to give a compound represented by formula (10) (referred to hereinafter as compound (10)):

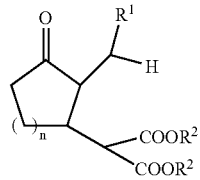

(10)

wherein n, $R^1$ and $R^2$ have the same meaning as defined above.

The compound (6) is allowed to react, preferably in 1-to 5-molar excess, more preferably in 1.2-to 2-molar excess, with the compound (5).

The basic catalyst includes an alkali metal such as sodium and potassium and an alkali metal alkoxide such as sodium alkoxide and potassium alkoxide. The catalyst is used in a molar ratio of preferably 0.005 to 0.2 to the compound (5). The solvent is preferably a polar solvent such as alcohol. The reaction temperature is preferably in the range of −10 to 30° C., more preferably in the range of 0 to 20° C.

Then, the resulting compound (10) can be reacted with water to produce the compound (7). Preferably, water is added dropwise to the reaction system in a molar ratio of 1 to 3 to the compound (10) during the reaction. The reaction temperature is preferably in the range of 150 to 250° C.

[Process for Producing the Compound (8)]

Using the compound (3) obtained by the above process as the starting material, the compound (8) useful as a perfume material and a physiological activator can be obtained by a general method known in the art.

For example, the compound (3) is subjected to dehydration reaction in the same manner as in production of the compound (7) to give the compound (4), and the compound (4) is subjected to isomerization reaction in the same manner to give the compound (5). Then, the compound (5) is reduced with hydrogen in the presence of a catalyst such as Pd/C to give a compound represented by formula (11) (referred to hereinafter as compound (11)).

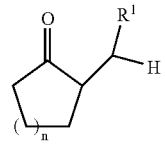

(11)

wherein n and $R^1$ have the same meaning as defined above.

The resulting compound (11) is subjected, for example, to Baeyer-Villiger oxidation with an oxidizing agent such as peracetic acid as described in JP-A 9-104681 to give the compound (8).

EXAMPLES

Example 1

Valeraldehyde having an acid value of 3.4 mg-KOH/g was used as the starting material. 117.6 g (1.4 mol) cyclopentanone, 125.2 g water and 2.8 g (0.033 mol) 48% NaOH were introduced into a 500-mL four-necked flask, then the mixture was cooled to 0° C. under stirring, and 72.4 g (0.84 mol) valeraldehyde was added dropwise at the same temperature over 4 hours. Thereafter, the mixture was stirred at the same temperature for 4 hours. After the reaction was finished, the mixture was neutralized with 17.4 g of 10% sulfuric acid and the organic layer was analyzed by gas chromatography. In this analysis, a methyl silicon column was used and diethylene glycol monoethyl ether (carbitol) was added as the standard. The result indicated that the reaction mixture contained 124.4 g (0.73 mol) 2-(1-hydroxy-n-pentyl)cyclopentanone (yield 87.4%) and 2.5 g (0.016 mol) 2-pentylidene cyclopentanone.

Example 2

Valeraldehyde having an acid value of 4.2 mg-KOH/g was used as the starting material. 719 g (8.55 mol) cyclopentanone, 320 g water and 3.5 g (0.042 mol) 48% NaOH were introduced into a 2-L four-necked flask, then the mixture was cooled to 15° C. under stirring, and 319 g (3.70 mol) valeraldehyde was added dropwise at the same temperature over 5 hours. Thereafter, the mixture was stirred at the same temperature for 2 hours. After the reaction was finished, the mixture was neutralized and analyzed in the same manner as in Example 1. The result indicated that the reaction mixture contained 557 g (3.27 mol) 2-(1-hydroxy-n-pentyl)cyclopentanone (yield 89.0%) and 6.8 g (0.044 mol) 2-pentylidene cyclopentanone.

Example 3

Valeraldehyde having an acid value of 3.4 mg-KOH/g was used as the starting material. 719 g (8.55 mol) cyclopentanone, 325 g water and 2.8 g (0.034 mol) 48% NaOH were introduced into a 2-L four-necked flask, then the mixture was cooled to 15° C. under stirring, and 337 g (3.91 mol) valeraldehyde was added dropwise at the same temperature over 5 hours. Thereafter, the mixture was stirred at the same temperature for 3 hours. After the reaction was finished, the mixture was neutralized and analyzed in the same manner as in Example 1. The result indicated that the reaction mixture contained 562 g (3.30 mol) 2-(1-hydroxy-n-pentyl)cyclopentanone (yield 85.0%) and 9.5 g (0.063 mol) 2-pentylidene cyclopentanone.

Example 4

Valeraldehyde having an acid value of 2.1 mg-KOH/g was used as the starting material. 199 g (2.37 mol) of cyclopentanone, 60 g of water and 1.2 g (0.014 mol) of 48% NaOH were introduced into a 500-mL four-necked flask. Then the mixture was cooled to 15° C. under stirring and 60 g (0.70 mol) of valeraldehyde was added dropwise at the same temperature over 5 hours. Thereafter, the mixture was stirred at the same temperature for 2 hours. After the reaction had finished, the mixture was neutralized and analyzed in the same manner as in Example 1. The result indicated that the reaction mixture contained 107 g (0.63 mol) of 2-(1-hydroxy-n-pentyl)cyclopentanone (yield 90.5%) and 2.0 g (0.013 mol) 2-pentylidene cyclopentanone.

Example 5

Valeraldehyde having an acid value of 8.6 mg-KOH/g was used as the starting material. 719 g (8.55 mol) cyclopentanone, 326 g water and 10.0 g (0.046 mol) 48% NaOH were introduced into a 2-L four-necked flask, then the mixture was cooled to 15° C. under stirring, and 319 g (3.70 mol) valeraldehyde was added dropwise at the same temperature over 5 hours. Thereafter, the mixture was stirred at the same temperature for 4 hours, but the non-converted valeraldehyde remained, and the yield was 65.3%.

Additional 15.8 g (0.19 mol) 48% NaOH was added thereto, and the mixture was stirred at the same temperature for 2 hours. After the reaction was finished, the mixture was neutralized and analyzed in the same manner as in Example 1. The result indicated that the reaction mixture contained 521 g (3.06 mol) 2-(1-hydroxy-n-pentyl)cyclopentanone (yield 83.8%) and 18.2 g (0.119 mol) 2-pentylidene cyclopentanone.

Comparative Example 1

Valeraldehyde having an acid value of 7.3 mg-KOH/g was used as the starting material. 178 g (2.14 mol) cyclopentanone, 80 g water and 0.62 g (0.007 mol) 48% NaOH were introduced into a 500-mL four-necked flask, then the mixture was cooled to 15° C. under stirring, and 80.4 g (0.93 mol) valeraldehyde was added dropwise at the same temperature over 5 hours. Thereafter, the mixture was stirred at the same temperature for 3 hours. After the reaction was finished, the mixture was neutralized and analyzed in the same manner as in Example 1. The result indicated that the reaction mixture contained 62.9 g (0.37 mol) 2-(1-hydroxy-n-pentyl)cyclopentanone (yield 40.0%) and 0.55 g (0.004 mol) 2-pentylidene cyclopentanone.

The reaction conditions and results in Examples 1 to 5 and Comparative Example 1 are collectively shown in Table 1.

TABLE 1

|  | Example 1 | Example 2 | Example 3 | Example 4 | Example 5 | Comparative example 1 |
|---|---|---|---|---|---|---|
| Acid value of valeraldehyde (mg-KOH/g) | 3.4 | 4.2 | 3.4 | 2.1 | 8.6 | 7.3 |
| Amount of valeraldehyde added(P) (mol) | 0.84 | 3.70 | 3.91 | 0.70 | 3.70 | 0.93 |
| Content (B) of carboxylic acid in valeraldehyde (mol) | 0.004 | 0.024 | 0.020 | 0.002 | 0.049 | 0.010 |
| Added amount of cyclopentanone (mol) | 1.40 | 8.55 | 8.55 | 2.37 | 8.55 | 2.14 |

TABLE 1-continued

|  | Example 1 | Example 2 | Example 3 | Example 4 | Example 5 | Comparative example 1 |
|---|---|---|---|---|---|---|
| Added amount(A) of NaOH (mol) | 0.033 | 0.042 | 0.034 | 0.014 | 0.236 | 0.007 |
| Amount of effective NaOH (A − B) (mol) | 0.029 | 0.019 | 0.014 | 0.012 | 0.187 | −0.003 |
| Reaction temperature (° C.) | 0 | 15 | 15 | 15 | 15 | 15 |
| Time of dropping of valeraldehyde (hr) | 4 | 5 | 5 | 5 | 5 | 5 |
| Aging time (hr) | 4 | 2 | 3 | 2 | 6 | 3 |
| Cyclopentanone/Valeraldehyde (molar ratio) | 1.7 | 2.3 | 2.2 | 3.4 | 2.3 | 2.3 |
| Added NaOH/Valeraldehyde (molar ratio) | 0.0394 | 0.0115 | 0.0087 | 0.0201 | 0.0637 | 0.0080 |
| Effectibe NaOH/Valeraldehyde*[1] (molar ratio) | 0.0342 | 0.0051 | 0.0035 | 0.0170 | 0.0505 | −0.0032 |
| Water/Cyclopentanone (weight ratio) | 1.06 | 0.45 | 0.45 | 0.30 | 0.45 | 0.45 |
| Content (Q) of 2-(1-hydroxy-n-pentyl) cyclopentanone (mol) | 0.73 | 3.27 | 3.30 | 0.63 | 3.06 | 0.37 |
| Yield (%)*[2] | 87.4 | 89.0 | 85.0 | 90.5 | 83.8 | 40.0 |

*[1]Difference between A and B (A − B) per mole of alkyl aldehyde
*[2]Yield(%) = [Q/(P − B)] × 100

Example 6

(a) Valeraldehyde having an acid value of 1.0 mg-KOH/g was used as the starting material. 112.3 g (1.34 mol) cyclopentanone, 50.0 g water and 0.24 g (0.0029 mol) 48% NaOH were introduced into a 500-mL four-necked flask, then the mixture was cooled to 15° C. under stirring, and 50.0 g (0.58 mol) valeraldehyde was added dropwise at the same temperature over 5 hours. Thereafter, the mixture was stirred at the same temperature for 2 hours. After the reaction was finished, the mixture was neutralized with 0.23 g (0.0025 mol) 105% condensed phosphoric acid and separated into two layers at 40° C. The resulting organic layer was 170.4 g, and the aqueous layer was 42.4 g. The pH of the aqueous layer was 5.5. The organic layer was analyzed in the same manner as in Example 1. The result indicated that the reaction mixture contained 86.0 g (0.505 mol) 2-(1-hydroxy-n-pentyl)cyclopentanone (yield 87.2%), 2.29 g (0.015 mol) 2-pentylidene cyclopentanone and 1.9 g (0.011 mol; content 1.1%) cyclopentanone dimer, and the aqueous layer contained 2.8 g cyclopentanone. 58.3 g cyclopentanone and 8 g water could be recovered by distillation from the organic layer. The phosphoric acid contained in the aqueous layer, as determined by titration with NaOH for converting it into trisodium phosphate, was 0.0062 mol.

(b) Then, the aqueous layer and the distilled fraction of (a) were introduced into a 500-mL four-necked flask and then 51.1 g cyclopentanone (1.34 mol including a re-used cyclopentanone) and 0.87 g (0.0105 mol) 48% NaOH, including NaOH for converting phosphoric acid contained in the aqueous layer to trisodium phosphate, were added thereto. The mixture was cooled to 15° C. under stirring, and 50.0 g (0.58 mol) valeraldehyde was added dropwise at the same temperature over 5 hours. Thereafter, the mixture was stirred at the same temperature for 2 hours. After the reaction was finished, the mixture was neutralized with 0.84 g (0.009 mol) 105% condensed phosphoric acid and separated into two phases at 40° C. The pH of the aqueous layer was 5.5. The resulting organic layer was 171.2 g, and the aqueous layer was 4.33 g. The organic layer was analyzed in the same manner as in Example 1. The result indicated that the reaction mixture contained 83.5 g (0.490 mol) 2-(1-hydroxy-n-pentyl)cyclopentanone (yield 84.6%) and 2.28 g (0.015 mol) 2-pentylidene cyclopentanone. 61.7 g cyclopentanone and 8.5 g water could be recovered by distillation from the organic layer. The phosphoric acid contained in the aqueous layer, as determined by titration with NaOH for converting it into trisodium phosphate, was 0.028 mol.

(c) The aqueous layer and the distilled fraction of (b) were introduced into a 500-mL four-necked flask and then 48.2 g cyclopentanone (1.34 mol including a re-used cyclopentanone) and 1.96 g (0.0236 mol) 48% NaOH, including NaOH for converting phosphoric acid contained in the aqueous layer to trisodium phosphate were added thereto. The mixture was cooled to 15° C. under stirring, and 50.0 g (0.58 mol) valeraldehyde was added dropwise at the same temperature over 5 hours. Thereafter, the mixture was stirred at the same temperature for 2 hours. After the reaction was finished, the mixture was neutralized with 1.89 g (0.0203 mol) 105% condensed phosphoric acid and separated into two phases at 40° C. The pH of the aqueous layer was 5.5. The resulting organic layer was 170.7 g, and the aqueous layer was 4.72 g. The organic layer was analyzed in the same manner as in Example 1. The result indicated that the reaction mixture contained 82.4 g (0.484 mol) 2-(1-hydroxy-n-pentyl)cyclopentanone (yield 83.5%) and 2.25 g (0.015 mol) 2-pentylidene cyclopentanone.

Comparative Example 2

(a) Valeraldehyde having an acid value of 7.5 mg-KOH/g was used as the starting material. 224.6 g (2.67 mol) cyclopentanone, 100 g water and 9.7 g (0.116 mol) 48% NaOH were introduced into a 1-L four-necked flask, then the mixture was cooled to 15° C. under stirring, and 100 g (1.16 mol) valeraldehyde was added dropwise at the same temperature over 5 hours. Thereafter, the mixture was stirred at the same temperature for 2 hours. After the reaction was finished, the mixture was neutralized with 9.3 g (0.100 mol) 105% condensed phosphoric acid and separated into two layers at 40° C. The resulting organic layer was 343.7 g, and the aqueous layer was 99.9 g. The pH of the aqueous layer was 5.5. The organic layer was analyzed in the same manner as in Example 1. The result indicated that the reaction mixture contained 165.8 g (0.974 mol) 2-(1-hydroxy-n-pentyl)cyclopentanone (yield 84.9%), 4.58 g (0.030 mol) 2-pentylidene cyclopentanone and 10.1 g (0.060 mol; content 2.9%) cyclopentanone dimer, and the aqueous layer contained 6.7 g cyclopentanone. 116.7 g cyclopentanone and 16 g water could be recovered by distillation from the organic layer. The phosphoric acid contained in the aqueous layer, as determined by titration with NaOH for converting it into trisodium phosphate, was 0.251 mol.

(b) Then, the aqueous layer and the distilled fraction in (a) were introduced into a 1-L four-necked flask, then 224.6 g cyclopentanone (2.67 mol including re-used cyclopentanone) and 22.6 g (0.271 mol) 48% NaOH including NaOH for converting phosphoric acid contained in the aqueous layer to trisodium phosphate were added thereto. The mixture was cooled to 15° C. under stirring, and 100 g (1.16 mol) valeraldehyde was added dropwise at the same temperature over 5 hours. Thereafter, the mixture was stirred at the same temperature for 2 hours. After the reaction was finished, the mixture was neutralized with 21.7 g (0.233 mol) 105% condensed phosphoric acid and separated into two phases at 40° C. The pH of the aqueous layer was 5.5. The resulting organic layer was 348.8 g, and the aqueous layer was 123.2 g. The organic layer was analyzed in the same manner as in Example 1. The result indicated that the reaction mixture contained 113.5 g (0.667 mol) 2-(1-hydroxy-n-pentyl)cyclopentanone (yield 58.1%) and 4.56 g (0.030 mol) 2-pentylidene cyclopentanone.

The reaction conditions and results in Example 6 and Comparative Example 2 are collectively shown in Table 2.

TABLE 2

|  | Example 6 | | | Comparative example 2 | |
| --- | --- | --- | --- | --- | --- |
|  | Step (a) | Step (b) | Step (c) | Step (a) | Step (b) |
| Acid value of valeraldehyde (mg-KOH/g) | 1 | 1 | 1 | 7.5 | 7.5 |
| Added amount(P) of valerardehyde (mol) | 0.58 | 0.58 | 0.58 | 1.16 | 1.16 |
| Content (B) of carboxylic acid in vareraldehyde (mol) | 0.00089 | 0.00089 | 0.00089 | 0.013 | 0.013 |
| Added amount of cyclopentanone (mol) | 1.34 | 1.34 | 1.34 | 2.67 | 2.67 |
| Added amount(A) of NaOH (mol) | 0.0029 | 0.0105 | 0.0236 | 0.116 | 0.271 |
| Amount (C) of NaOH in recovered aqueous layer (mol) |  | 0.0024 | 0.0107 |  | 0.098 |
| Amount (D) of catalytic*[1] (mol) | 0.0029 | 0.0066 | 0.0067 | 0.116 | 0.117 |
| Amount of effective NaOH (D − B) (mol) | 0.0020 | 0.0057 | 0.0058 | 0.103 | 0.104 |
| Added amount of phosphoric acid (mol) | 0.0025 | 0.0090 | 0.0203 | 0.100 | 0.233 |
| Amount of phosphoric acid in recovered aqueous layer (mol) | 0.0021 | 0.0075 | 0.017 | 0.084 | 0.193 |
| Amount(E) of NaOH for converting phosphoric acid into Na salt (mol) | 0.0062 | 0.028 |  | 0.251 |  |
| Reaction temperature (° C.) | 15 | 15 | 15 | 15 | 15 |
| Time of dropping of valeraldehyde (hr) | 5 | 5 | 5 | 5 | 5 |
| aging time (hr) | 2 | 2 | 2 | 2 | 2 |
| Cyclopentanone/Valeraldehyde (molar ratio) | 2.3 | 2.3 | 2.3 | 2.3 | 2.3 |
| Added NaOH/Valeraldehyde (molar ratio) | 0.0050 | 0.0180 | 0.0406 | 0.1001 | 0.2332 |
| Effective NaOH/Valeraldehyde*[2] (molar ratio) | 0.0034 | 0.0099 | 0.0100 | 0.0887 | 0.0896 |
| Water/Cyclopentanone (weight ratio) | 0.445 | 0.445 | 0.445 | 0.445 | 0.445 |
| Content (Q) of 2-(1-hydroxy-n-pentyl)cyclopentanone (mol) | 0.505 | 0.490 | 0.484 | 0.974 | 0.667 |
| Yield (%)*[3] | 87.2 | 84.6 | 83.5 | 84.9 | 58.1 |
| Cyclopentanone dimer content(%) | 1.1 | — | — | 2.9 | — |

*[1]D = A + C − (E in the previous step)
*[2]Amount of effective catalyst (D − B) per mol of alkyl aldehyde
*[3]Yield(%) = [Q/(P − B)] × 100

As is evident from Table 2, the difference between A and B (A−B) in step (a) in Example 6 was 0.06 mol or less per mol of aldehyde, while that of step (a) in Comparative Example 2 was higher than 0.06 mol per mol of aldehyde. In Comparative Example 2, therefore, the cyclopentane dimer content in step (a) was high and the yield in step (b) where the aqueous layer was used again was lower than that of Example 6.

Example 7

The reaction in Example 1 was carried out twice, the product was distilled to recover cyclopentanone and water, then 0.0206 mol oxalic acid was added to 1.01 mol 2-(1-hydroxy-n-pentyl)cyclopentanone and 0.022 mol 2-pentylidene cyclopentanone from the product, and the mixture was reacted at 120° C. The reaction mixture contained 141 g (0.93 mol) 2-pentylidene cyclopentanone. Its filtered product was dissolved in 153 g n-butanol and heated at 130° C., and then a mixture of 14.5 g (0.15 mol) 3-picoline and 10.5 g (0.1 mol) 35% hydrochloric acid was added dropwise at the same temperature over 30 minutes. Thereafter, the mixture was stirred at the same temperature for 3.5 hours. After the reaction was finished, the mixture was cooled to room temperature and neutralized with an aqueous sodium hydroxide solution, and the organic layer was analyzed. The result indicated that the reaction mixture contained 118 g 2-pentyl-2-cyclopentenone. The yield in this isomerization reaction was 83%.

From this reaction mixture, 95 g (0.6 mol) 2-pentyl-2-cyclopentenone was purified. Separately, 118 g (0.9 mol) dimethyl malonate was dissolved in 38 g anhydrous methanol in a nitrogen atmosphere and then cooled to 0° C., and 6.5 g (0.036 mol) sodium methoxide (30% methanol) was added thereto. 95 g (0.6 mol) 2-pentyl-2-cyclopentenone obtained above was added dropwise thereto at 0° C. over 2 hours. Thereafter, the mixture was stirred at the same temperature for 3 hours. Thereafter, the unreacted dimethyl malonate was distilled away under reduced pressure, whereby 160 g Michael addition product was obtained.

The Michael addition product obtained above was added to a reaction device equipped with a distillation tube and then heated at 215° C., and water was added dropwise at a rate of 3.2 g/h (2%/h). By adding water dropwise, the mixture was reacted for 4 hours at 215° C. while generated carbon dioxide and methanol were distilled away. After the reaction was finished, 123 g methyl 3-oxo-2-pentylcyclopentylacetate was obtained in 126 g crude product. The yield in the whole process was 60%.

The crude product was refined by distillation to give methyl 3-oxo-2-pentylcyclopentylacetate having a fruity jasmine-like aroma, which was also excellent as a perfume material.

Comparative Example 3

The reaction in Comparative Example 1 was carried out 3 times, the product was distilled to recover cyclopentanone and water, then 0.0206 mol oxalic acid was added to 1.11 mol 2-(1-hydroxy-n-pentyl)cyclopentanone and 0.012 mol 2-pentylidene cyclopentanone from the product, and the mixture was reacted at 120° C. Thereafter, the reaction was carried out in the same manner as in Example 7, to give methyl 3-oxo-2-pentylcyclopentylacetate. As a result, the yield in the whole process was 28%.

The invention claimed is:

1. A process for producing a 2-(1-hydroxyalkyl)cycloalkanone and/or a 2-(1-hydroxyaryl)cycloalkanone represented by formula (3), which comprises the steps of subjecting a cycloalkanone, and an aldehyde represented by formula (2) comprising a carboxylic acid represented by formula (1), to aldol condensation in the presence of water and a basic catalyst, wherein the molar amount of the basic catalyst A added is not less than the molar amount of the carboxylic acid (1) represented by the formula (1) B and the difference between A and B is 0.06 mol or less per mol of the aldehyde (2)

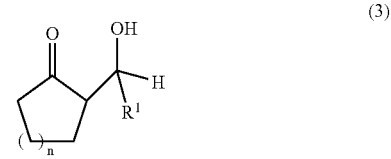

wherein n is an integer of 1 or 2, and $R^1$ represents a hydrogen atom or a C1 to C8 linear or branched alkyl group or a substituted or unsubstituted aryl group wherein an aqueous layer obtained after the aldol condensation reaction is used again, wherein an aqueous layer recovered through pH adjustment with an acid and separation of the layer after the aldol condensation reaction is used again.

2. The process according to claim 1, wherein the basic catalyst is added in such an amount as to neutralize or alkalize (to pH 7 or more) the aqueous layer before the aqueous layer is used again.

* * * * *